United States Patent [19]

Laine

[11] 4,292,242
[45] Sep. 29, 1981

[54] PRODUCTION OF AMINES

[75] Inventor: Richard M. Laine, Mountain View, Calif.

[73] Assignee: SRI International, Menlo Park, Calif.

[21] Appl. No.: 181,419

[22] Filed: Aug. 26, 1980

Related U.S. Application Data

[63] Continuation-in-part of Ser. No. 967,028, Dec. 6, 1978, Pat. No. 4,226,845.

[51] Int. Cl.$^3$ .............. C07C 85/08; C07C 85/18; C07D 207/06; C07D 239/02
[52] U.S. Cl. .............. 260/326.8; 260/326.9; 260/347.7; 546/176; 546/184; 546/329; 564/307; 564/373; 564/374; 564/381; 564/382; 564/445; 564/446; 564/467; 564/471; 564/473
[58] Field of Search .............. 260/326.8; 546/176, 546/329; 564/307, 382, 445, 467, 473, 485

[56] References Cited

U.S. PATENT DOCUMENTS

| | | | |
|---|---|---|---|
| 2,542,747 | 2/1951 | Barrick | 564/485 |
| 3,234,283 | 2/1966 | Finch et al. | 564/467 |
| 3,513,200 | 5/1970 | Biale | 564/382 X |
| 4,096,150 | 6/1978 | Berthoux et al. | 564/307 X |
| 4,144,191 | 3/1979 | Hartwell et al. | 252/428 |

FOREIGN PATENT DOCUMENTS 891067 3/1962 United Kingdom ............. 564/307

OTHER PUBLICATIONS

Iqbal, "Helvetica Chimica Acta", vol. 54, pp. 1440-1445 (1971).

*Primary Examiner*—John Doll
*Attorney, Agent, or Firm*—Edward B. Gregg; Donovan J. DeWitt

[57] ABSTRACT

Aminomethylation of olefins which employs a homogeneous catalyst which is a solution in a suitable solvent of mixed ruthenium and iron carbonyls. The overall reaction may be represented as follows:

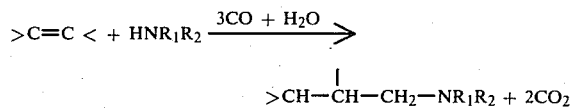

where $R_1$ and $R_2$ are hydrogen or essentially hydrocarbon groups. The reaction proceeds by way of an aldehyde intermediate. Accordingly, the starting material may be an aldehyde instead of an olefin.

6 Claims, No Drawings

PRODUCTION OF AMINES

The Government has rights in this invention pursuant to Grant No. 77-21246 and IPA No. 0016 awarded by the National Science Foundation.

This application is a continuation-in-part of my co-pending application, Ser. No. 967,028, filed Dec. 6, 1978, entitled "IMPROVEMENTS IN THE WATER GAS SHIFT REACTION AND IN THE HYDROFORMYLATION AND HYDROHYDROXYMETHYLATION REACTIONS" now U.S. Pat. No. 4,226,845.

This invention relates to the aminomethylation of olefins whereby the olefinic group

is converted to the group

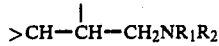

wherein $R_1$ and $R_2$ are variously hydrogen, hydrocarbon groups or the latter substituted by hetero atoms or groups provided they do not significantly inhibit the reactions involved and are otherwise compatible. The nitrogen may be part of a ring as in piperidine. Inasmuch as the overall reaction starting with the olefin and using carbon monoxide and water includes the production of an aldehyde intermediate, the starting material may be an aldehyde but preferably it is an olefin, in which event the aldehyde is not isolated.

In my copending application mentioned above there is described the use of a mixed ruthenium/iron carbonyl catalyst for the hydroformylation and hydrohydroxymethylation reactions of olefins with carbon monoxide and water, or with carbon monoxide and hydrogen. In that application, it is pointed out that the ruthenium/iron carbonyl catalyst is superior to either the ruthenium carbonyl or the iron carbonyl alone in several respects.

In a paper by Iqbal published in Helvetica Chemica Acta, Volume 54, pages 1440 to 1445 (1971), the catalytic aminomethylation of olefins is described employing a rhodium oxide catalyst, an iron carbonyl catalyst and a mixed rhodium oxide/iron carbonyl catalyst. (Rhodium carbonyls form during the reaction.) The overall reaction is described as follows:

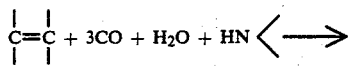

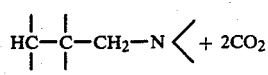

The mixed rhodium/iron carbonyl catalyst of Iqbal is said to be superior to the rhodium carbonyl catalyst alone and to the iron carbonyl catalyst alone. However, this mixed rhodium carbonyl/iron carbonyl catalyst is less selective and has other disadvantages, among which are the following: The rhodium carbonyl/iron carbonyl catalyst is not stable and is prone to decompose; its use results in carboxy amide by-products; and it reduces some of the intermediate aldehyde to an alcohol. Also, in the case of an olefin having a terminal vinyl group, $-CH=CH_2$, a considerable proportion of the amino product is branched chain, thus

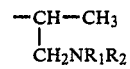

rather than straight chain, thus

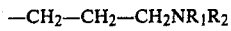

The straight chain products are more important commercially.

It is an object of the present invention to provide improved methods of aminomethylation which are more selective and lead to fewer unwanted by-products such as alcohols and carboxy amides.

It is a further object to provide a mixed metal carbonyl catalyst which is stable and whose use results in higher yields of the desired amine.

The above and other objects will be apparent from the ensuing description and the appended claims.

In accordance with the present invention a mixed ruthenium carbonyl/iron carbonyl catalyst is employed for the aminomethylation of olefins. By that means greater selectivity and other advantages result such as greater catalyst stability and better yields.

The following specific example will serve to illustrate the practice and advantages of the invention: 4.72 grams (6.0 ml.) of methanol, 1.15 gram (1.0 ml.) of 3.0 normal aqueous solution of KOH, 2.53 grams (4.0 ml., 36 mmol) of 1-pentene and 1.0 ml. (10 mmol) of piperidine were mixed. Also included was 2.00 mmol of n-butyl ether or ethoxyethanol as an internal standard for chromatographic analysis. To each such batch was added a catalyst as indicated in Table I below. This mixture was placed in a quartz-lined Parr general purpose bomb reactor. The reactor, which contained the mixture and a magnetic stir bar, was sealed and degassed by three 800-psi pressurization/depressurization cycles with CO. The reaction was then charged to 800 psi CO, heated with magnetic stirring at 150° to 0.5 hour, cooled to 0° and depressurized. The reactor was opened and 3.0 ml of tetrahydrofuran was added. The solution was stirred for 10 minutes and analyzed. This procedure was employed in each of the examples set forth in Table I.

TABLE I

| | Catalyst Precursor | Aminomethylation Turnover Rate | Formamide Turnover Rate |
|---|---|---|---|
| (1) | $Fe_3(CO)_{12}$ | 8 (76) | 14 |
| (2) | $Ru_3(CO)_{12}$ | 20 (98) | 12 |
| (3) | $[(C_6H_5)_2P]Rh(CO)Cl$ | 5 (88) | 13 |
| (4) | $Rh_6(CO)_{16}$ | 70 (83) | 6 |
| (5) | $Rh_6(CO)_{16}$ | 60 (84) | 5 |
| (6) | $Rh_6(CO)_{16}/Fe_3(CO)_{12}$ | 84 (78) | 2 |
| (7) | $Rh_6(CO)_{16}/Fe_3(CO)_{12}$ | 90 (78) | 1 |
| (8) | $Fe_3(CO)_{12}$ | 60 (94) | 5 |
| (9) | $Fe_3(CO)_{12}/Ru_3(CO)_{12}$ | 70 (94) | 3 |
| (10) | $Fe_3(CO)_{12}/Ru_3(CO)_{12}$ | 70 (93) | 4 |

Referring to the table above, the following explanation is provided: By "Catalyst Precursor" is meant the carbonyls as purchased. The proportions of metal to CO under the conditions of reaction are unknown except that they are present in the form of carbonyls. In item (5) the quantity of catalyst was 0.05 mmol. In item (7) the molar ratio of rhodium and iron carbonyls was 0.05 and 0.10 mmols, respectively. In item (8) the molar ratio of ruthenium and iron carbonyls was 0.075 and 0.025 mmols, respectively. In item (9) the molar ratio of ruthenium and iron carbonyls was 0.025 mmol and 0.075 mmol, respectively. In items (6) and (9) the molar ratios were equal.

Turnover rates are moles of the indicated product per mole of catalyst precursor. Reaction time in all cases was 0.5 hour. The numbers in parentheses are percentages of straight chain amine, i.e. normal N-hexyl piperidine.

Among olefins which may be employed are straight and branched chain olefins of the aliphatic series containing, for example, 2 to 20 carbon atoms, for example, ethylene, propylene, the butenes, the pentenes, the hexenes, etc.; cycloaliphatic olefins such as cyclohexene, cyclopentene, etc. including those in which the unsaturated ring is substituted by alkyl groups; aromatic substituted olefins such as styrene, allyl benzene and 2-phenyl-2-butene; indene, vinyl pyridines, vinyl furans, vinyl quinolines, vinyl pyrroles, etc. Hetero atoms or groups may be present in any of these olefins provided they do not interfere with the reaction or react destructively with the catalyst, the reactants, the solvent or the end product.

Where aldehydes constitute the starting material they may be similarly diverse including, for example, the straight and branched chain aliphatic series of aldehydes containing 1 to 20 carbon atoms attached to the aldehyde group and which may be straight chain or branched chain; cycloaliphatic aldehydes; aromatic aldehydes such as benzaldehyde, etc. Substituted aldehydes of any of the classes mentioned above may be used which are substituted by a hetero atom or group provided the same is compatible as defined above.

Among amines that may be used are the straight and branched chain aliphatic series, e.g. $C_1$ to $C_{20}$ alkyl amines including primary amines and secondary amines, also ammonia. Further, cycloaliphatic amines may be used such as cyclohexyl amine, tetrahydrofuranyl amines, piperidinyl amines, etc. Also, amines may be used in which the amino nitrogen forms part of a cycloaliphatic ring such as, for example, piperidine, pyrrolidine, steroidal amines and alkaloidal amines. Also, aromatic amines such as aniline, xylidine, toluidine, etc. may be used. As in the case of the olefins and the aldehydes described above, hetero atoms and groups may be present provided they meet the compatibility requirements referred to above.

In connection with the catalyst the molar proportions of ruthenium and iron may range from 1 to 99% of ruthenium to 99 to 1% of iron. Preferably the range is about 10% to 90% of ruthenium and 90% to 10% of iron, most advantageously 25% to 75% ruthenium and 75% to 25% iron.

The catalyst may be purchased as a mixture of iron and ruthenium carbonyls or the separate metal carbonyls may be purchased and mixed in the desired proportions. The catalyst may also be prepared in situ from any salts or oxides of the metals during the course of the aminomethylation reaction. The metals may be in any valence state inasmuch as the carbon monoxide reduces the metal ions to their lowest valence state.

The reaction may be carried out at temperatures of 80° to 350° C. at pressures of 1 atmosphere to 1,000 atmospheres of carbon monoxide and water along with other gases. The reaction as described in the examples above was carried out in batch fashion in a bomb but continuous procedures may be employed.

The catalyst may be employed in amounts of 0.01 mole or less to 1.0 mole or more percent based upon the olefin or, if an aldehyde is used as a starting material, based upon the aldehyde.

Suitable solvents are various alcohols, e.g. methanol, ethanol, ethoxyethanol, ethylene glycol; ethers such as dioxanes, glymes, diglymes, crown ethers, cryptates. DMSO, DMF, sulfolane, pyrolidones, triethanol amines; etc. The solvent should be chosen so that it dissolves the catalyst, reactants and reaction product and is not destructive of or incompatible with the catalyst, the reactants and the reaction product.

The reaction is carried out under alkaline conditions, preferably using potassium, sodium, caesium or rubidium hydroxide, carbonate or bicarbonate of mixtures thereof. Hydrogen may be used instead of water where the starting material is an aldehyde and the base is an alkali metal (Na, K, Cs or Rb) alkoxide (e.g. ethoxide) or phenolate. In such instances, i.e. use of $CO+H_2$ rather than $CO+H_2O$, if the starting material is an olefin, yields of the desired amines are diminished and the production of other compounds increases.

The mechanism of the reaction where the olefin is of the type $>C=CHR$ (R being hydrogen or an organic group) is believed to be as follows:

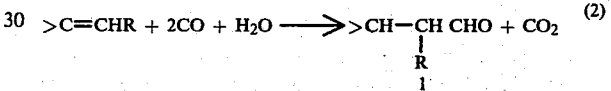

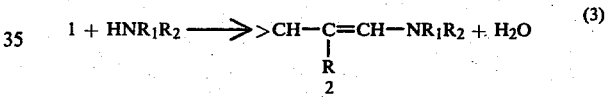

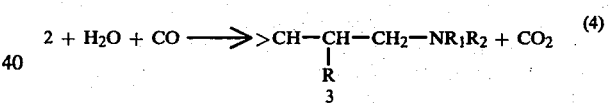

If the olefin is of the type

wherein $R_3$, $R_4$, $R_5$ and $R_6$ are organic groups, i.e. the olefinic group is fully substituted and no hydrogen atoms are attached to the olefinic carbon atoms, the mechanism (using tetramethyl ethylene as an example) is believed to be as follows:

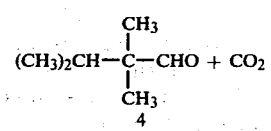

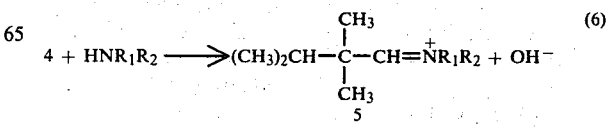

$$5 + CO + H_2O \longrightarrow \quad (7)$$

$$(CH_3)_2-CH-\underset{\underset{CH_3}{|}}{\overset{\overset{CH_3}{|}}{C}}-CH_2NR_1R_2 + CO_2 + H^+$$
$$6$$

It will be apparent that a new and useful method of aminomethylation has been provided; also a new and useful method of producing amines from aldehydes has been provided.

I claim:

1. In the production of an amine by the aminomethylation of an olefin wherein an olefin is reacted with ammonia, a primary amine or a secondary amine in the presence of carbon monoxide and water or hydrogen, and in the production of an amine by reaction of an aldehyde with ammonia, a primary amine or a secondary amine in the presence of carbon monoxide and water or hydrogen, and wherein a homogeneous catalyst in the form of a solution of a catalyst in a solvent is used, the improvement which comprises employing a mixed ruthenium carbonyl/iron carbonyl as a catalyst.

2. The improvement of claim 1 wherein the reactant with the amine is an olefin.

3. The improvement of claim 2 wherein the olefin has a terminal vinyl group and the resulting amine product is predominantly of the type $$>CH-CH_2-CH_2-NR_1R_2$$

wherein $R_1$ and $R_2$ are hydrogen or organic groups and may form parts of a cyclic structure.

4. The improvement of claim 1 wherein the molar ratio of iron to ruthenium is about 25% to 75% iron and 75% to 25% ruthenium.

5. The improvement of claim 2 wherein the reactants are the olefin, carbon monoxide and water and the solution is made alkaline with the hydroxide, carbonate or bicarbonate of sodium, potassium, caesium or rubidium.

6. The improvement of claim 2 wherein the reactants are an olefin, carbon monoxide and hydrogen and the solution is made alkaline by an alkoxide or phenolate of sodium, potassium, caesium or rubidium.

* * * * *